(12) United States Patent
Sonehara et al.

(10) Patent No.: US 8,004,673 B2
(45) Date of Patent: Aug. 23, 2011

(54) PHOTOMETRIC INSTRUMENT

(75) Inventors: Tsuyoshi Sonehara, Kokubunji (JP);
Satoshi Takahashi, Hitachinaka (JP);
Tomoyuki Sakai, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 318 days.

(21) Appl. No.: 12/292,444

(22) Filed: Nov. 19, 2008

(65) Prior Publication Data

US 2009/0128807 A1    May 21, 2009

(30) Foreign Application Priority Data

Nov. 21, 2007 (JP) .................................. 2007-301274
Aug. 28, 2008 (JP) .................................. 2008-219804

(51) Int. Cl.
*G01J 3/30* (2006.01)
(52) U.S. Cl. ....................................................... 356/317
(58) Field of Classification Search .............. 356/72–73, 356/317–318; 250/458.1–461.2
See application file for complete search history.

(56) References Cited

U.S. PATENT DOCUMENTS

| | | | |
|---|---|---|---|
| 6,180,415 B1 * | 1/2001 | Schultz et al. | 356/317 |
| 7,397,559 B1 * | 7/2008 | Bratkovski | 356/301 |
| 2005/0053974 A1 | 3/2005 | Lakowicz et al. | |
| 2006/0170918 A1 * | 8/2006 | Nishiuma | 356/318 |
| 2007/0248991 A1 | 10/2007 | Ojima et al. | |
| 2008/0088845 A1 * | 4/2008 | Ke et al. | 356/445 |
| 2008/0278722 A1 * | 11/2008 | Cunningham et al. | 356/317 |

FOREIGN PATENT DOCUMENTS

| | | |
|---|---|---|
| JP | 9-257813 | 3/1996 |
| JP | 2005-70031 | 6/2004 |

OTHER PUBLICATIONS

Takashi Funatsu et al., Imaging of Single Fluorescent Moleculres and individual ATP Turnovers by Single Myosin Molecules in Aqueous Solution:, Letters of Nature, vol. 374, Apr. 6, 1995, pp. 555-559.
European Search Report for corresponding European Patent Application No. 08020249.2-2217/2063258.

* cited by examiner

*Primary Examiner* — Kara E Geisel
(74) *Attorney, Agent, or Firm* — Stites & Harbison PLLC; Juan Carlos A. Marquez, Esq.

(57) ABSTRACT

A metallic structure is provided on a surface of a substrate. A component having a longer wavelength than excitation light is detected from luminescence from fixation positions of biomolecules and emitted from a material other than the biomolecules, and is used for photometrical analysis. As the structure, usable is a particulate (a metallic structure of a size not larger than a wavelength of the excitation light), a minute protrusion, or a thin film with minute apertures, which are made of a metal such as gold, chrome, silver or aluminum. In the case of the particulate or the minute protrusion, photoluminescence of the structure is detected with a biomolecule being fixed thereon. In the case of the thin film with minute apertures, Raman scattered light of specimen solution around the biomolecules, and photoluminescence of the metallic structure near the biomolecules are detected with biomolecules being fixed in the apertures.

19 Claims, 14 Drawing Sheets

(1)

(2)

(3)

(4)

PHOTOMETRIC INSTRUMENT

CLAIM OF PRIORITY

The present application claims priority from Japanese patent application JP 2007-301274 filed on Nov. 21, 2007 and JP 2008-219804 filed on Aug. 28, 2008, the content of which is hereby incorporated by reference into this application.

BACKGROUND OF THE INVENTION

1. Field of the Invention

The present invention relates to a photometric instrument. For example, it relates to a photometric instrument which photometrically analyzes biopolymer by irradiating the biopolymer with light.

2. Description of the Related Art

Conventionally, there have been proposed methods of observing a configuration of an object, which is placed on a surface of a substrate, by irradiating the object with excitation light. In Japanese Patent Application Publication No. Hei 9-257813 (hereinafter, JP-A 9-257813), for example, there is described an instrument which irradiates a transparent substrate with excitation light emitted from an excitation source, generates evanescent waves on a surface of the substrate by totally reflecting the excitation light inside the substrate, and detects scattered light of the evanescent waves from a specimen on the substrate. In the instrument described in JP-A 9-257813, however, the scattered light is not spectrally separated.

In addition, for example, Japanese Patent Application Publication No. 2005-70031 (hereinafter, JP-A 2005-70031) describes an instrument for spectrally separating fluorescence and scattered light which come from specimen components excited by evanescent waves. In the instrument described in JP-A 2005-70031, however, the specimen components are not fixed on a boundary surface of a flow path.

On the other hand, there is an instrument which, with a plurality of biomolecules being fixed to a surface of a substrate, generates evanescent waves in a given range on the substrate surface as in the case with JP-A 9-257813, and performs imaging of luminescence of the biomolecules excited by the evanescent waves. Although luminescence of biomolecules includes scattered light and fluorescence, fluorescence is observed in general because scattered light of biomolecules is extremely weak. First, non-fluorescent biomolecules are fixed on the substrate, then, reaction solution containing fluorescent molecules is flown onto the substrate, and luminescence from fixation positions of the biomolecules is observed. Thereby, bonding reactions of the biomolecules and the molecules in the reaction solution can be observed. For example, unlabeled single-stranded DNA is fixed on the substrate at the beginning, and a sequence of the fixed DNA can be read by: introducing thereon a reaction solution containing fluorescent-labeled base species respectively labeled with different phosphors; and spectrally separating fluorescence originating from molecule fixation positions while bonding the single-stranded DNA to its complementary bases.

SUMMARY OF THE INVENTION

In an instrument for analyzing biomolecules through imaging of fluorescence of the biomolecules fixed on a surface of a substrate, generally, different kinds of biomolecules are respectively fixed on different spots on the substrate, and fluorescence from the respective spots is separated and then detected through the imaging. In order to analyze many kinds of biomolecules in minimal time, and to reduce a consumption of reagents, it is favorable to form spots so that the biomolecules can be fixed on the substrate as densely as possible to the extent allowing optical resolution thereof. Additionally, so as to reduce a consumption of reagents per spot, it is more advantageous to fix a smaller number of biomolecules in one spot, and the number is ideally one. As described in Funatsu et al., Nature Vol. 374, 555-559 (1995), although a fluorescence detection method has a sufficient sensitivity for detecting even one molecule, a spectral imaging method causing only a smaller loss is preferable for the purpose of obtaining a favorable S/N ratio in spectroscopically detecting fluorescence from a small number of molecules. For this reason, preferable methods for this purpose are a dispersive spectral imaging method using a dispersing element such as a prism or a diffraction grating, and a method (dichroic/multi-sensor spectral imaging method) in which multiple image sensors respectively acquires images from light spectrally separated by a dichroic mirror.

The dispersive spectral imaging method, however, has the following problem because a change in wavelength of fluorescence is converted into a change in spot image positions in a fluorescence image. More specifically, there is a case where, even though one species of phosphors of plural species having different luminous wavelengths have emitted fluorescence, which species of the phosphors has emitted the fluorescence cannot be identified. In this case, the dispersive spectral imaging method cannot determine which spot the fluorescence has been emitted from, based on spot positions in the fluorescence image, and thus fails to identify the species of the phosphors having emitted the fluorescence.

On the other hand, in the dichroic/multi-sensor spectral imaging method, in multiple images obtained by the respective sensors, luminescence from the same spot is placed at the same position regardless of species of phosphors, ideally. In reality, however, images of fluorescence from the same spot are inevitably positioned slightly differently from one sensor to another because of such reasons as differences in imaging magnification, incompletion of optical adjustments, chromatic aberrations, and individual differences among the sensors. Additionally, because an S/N ratio of fluorescence detection from a small number of molecules is not necessarily sufficiently high, a center position of a spot image may vary over time. In addition, when the spots are implemented at the maximum density allowed by its optical resolution, the dichroic/multi-sensor spectral imaging method may also cause an error in judgment on which spot on the substrate a spot image originates from.

As described above, in the highly sensitive spectral imaging methods, it has been difficult to highly-accurately associate, as a pair, a spot in a fluorescence image with a spot on a specimen substrate.

The present invention was made in consideration of the above described situations, and is configured to provide photometrical analysis based on a spectral imaging method capable of highly-accurately associating spot images with spots on a specimen (identifying correspondences therebetween) and also highly-accurately determining a phosphor species having become luminous.

In order to solve the above problems, in the present invention, a metallic structure is provided on a surface of a substrate, and a component having a longer wavelength than excitation light is detected out of luminescence which originates from fixation positions of biomolecules and is emitted from a material other than the biomolecules. Thus detected component is used for photometrical analysis. As the structure, any one of a particulate (a metallic structure forming a size not larger than a wavelength of the excitation light), a minute protrusion, and a thin film with minute apertures, which are made of a metal such as gold, chrome, silver or aluminum, can be used. In the case using the particulate or the minute protrusion, photoluminescence of the metallic structure is detected with a biomolecule being fixed on the metallic structure. In the case using the thin film with minute apertures, Raman scattered light of a specimen solution around the biomolecules, and photoluminescence of the metallic structure in the vicinities of the biomolecules are detected with biomolecules being fixed in the apertures.

That is, a photometric instrument according to the present invention includes: a substantially transparent substrate provided with a plurality of structures on each of which a biomolecule is fixed; at least one light source for irradiating the substrate with excitation light; a light separating portion for spectrally separating light emitted from the structures; a sensor portion for detecting light spectrally separated by the light separating portion; and a processing portion for processing light detected by the sensor portion. The processing portion typically processes an image obtained by the sensor portion. The sensor portion detects, based on a result of the spectral separation of the light, light having a longer wavelength than the excitation light, and the processing portion generates positional information of the structures based on the presence or absence of light having a longer wavelength than the excitation light. The substrate can be irradiated by the excitation light so as to generate evanescent waves from the substrate.

Note that the sensor portion may detect both of a part having longer wavelengths than the excitation light, and a part having the same wavelength as the excitation light, out of luminescence from the structures excited by the evanescent waves. In this case, the processing portion generates positional information of the structures based on the presence or absence of light having the same wavelength as the excitation light.

Additionally, the light separating portion is constituted of a dispersing element, a plurality of dichroic mirrors, or the like. In the case where the light separating portion is constituted of the dichroic mirrors, the sensor portion is constituted of a plurality of image sensors.

Furthermore, the processing portion computes a difference between a first image detected when a biomolecule is not luminous, and a second image detected when the biomolecule is luminous. Then, by comparing this difference and the first image, it determines a species of the biomolecule having become luminous.

Additionally, the sensor portion detects light resulting from overlapping of light emitted from the structures with light emitted from biomolecules. Then, the processing portion may generate the positional information by using, as background light, the light resulting from the overlapping. Additionally, the processing portion may determine species of the biomolecules based on relative positions of parts in the light resulting from the overlapping, the parts being brighter than surroundings thereof.

Further characteristics of the present invention will become obvious hereinbelow by the preferred embodiments of the present invention and the accompanying drawings.

According to the photometrical analyze based on the spectral imaging method of the present invention, it is possible to associate spot images with spots on a specimen (identifying correspondences therebetween) and to judge a phosphors species having become luminous with high accuracy.

DESCRIPTION OF THE PREFERRED EMBODIMENTS

Figure 1:
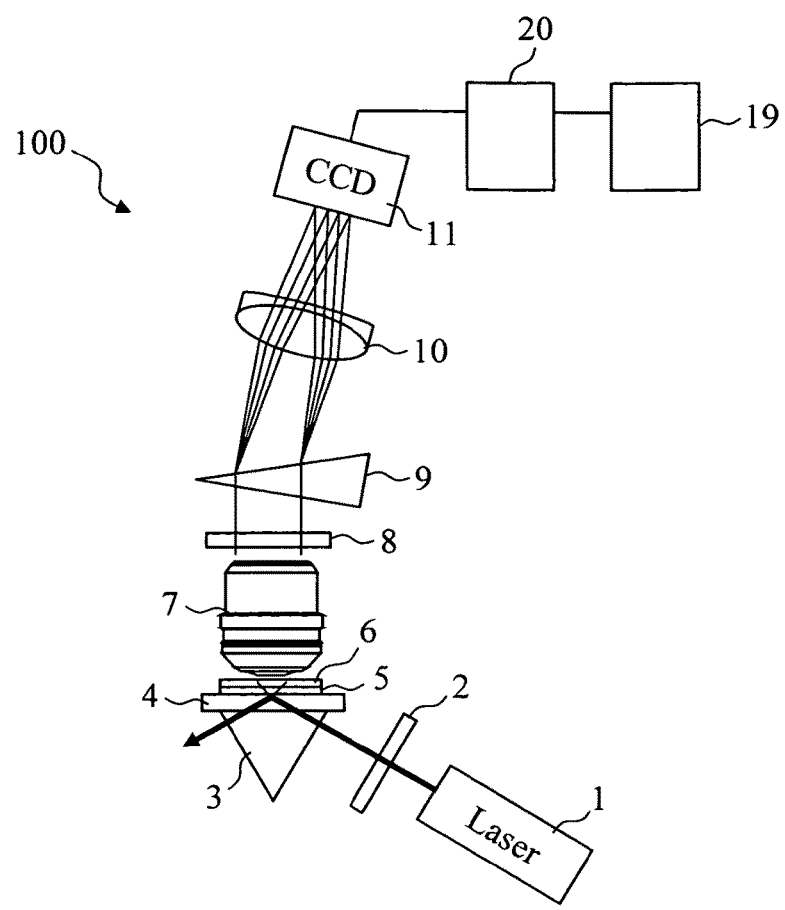
FIG. 1 is a view showing a schematic constitution of a photometric instrument according to a first embodiment of the present invention.

The present invention relates to an analysis technology for qualitatively detecting, or for quantifying, biomolecules by generating evanescent waves on a surface of a substrate made of a transparent material, then, by means of the evanescent waves, exciting the biomolecules labeled with fluorescent marks in a specimen solution that is supplied on a surface of the substrate, and then detecting fluorescence resultingly emitted from the biomolecules.

According to embodiments of the present invention, a high S/N ratio can be obtained by long-time exposure because photoluminescence from a metallic structure, and Raman scattering of the solution do not fade away whereas fluorescence from biomolecules fades away within a few minutes. As a result, a highly accurate spot position standard and a wavelength standard can be obtained as compared to the case where fluorescence from biomolecules is used for the same purpose.

Hereinbelow, the embodiments of the present invention will be described in detail with reference to the accompanying drawings. However, it should be noted that these embodiments are merely examples for achieving the present invention, and do not limit the technical scope of the present invention. Additionally, constitutional elements common to the respective drawings are provided with the same reference numerals.

First Embodiment

1. Constitution of Photometric Instrument

FIG. 1 is a view showing a schematic constitution of a photometric instrument 100 according to a first embodiment of the present invention. In FIG. 1, after spectral purity thereof is enhanced by an excitation filter 2, excitation light emitted from an excitation source 1 enters a prism 3 and then enters a substrate 4. A space between the prism 3 and the substrate 4 is filled with matching oil, whereby total reflection is prevented from occurring on interfaces of these. The excitation light having entered the substrate 4 is totally reflected by an upper surface thereof, and generates evanescent waves on a surface of the substrate. A space between the upper surface of the substrate 4 and a cover glass 6 is filled with a reaction solution 5.

Figure 5:
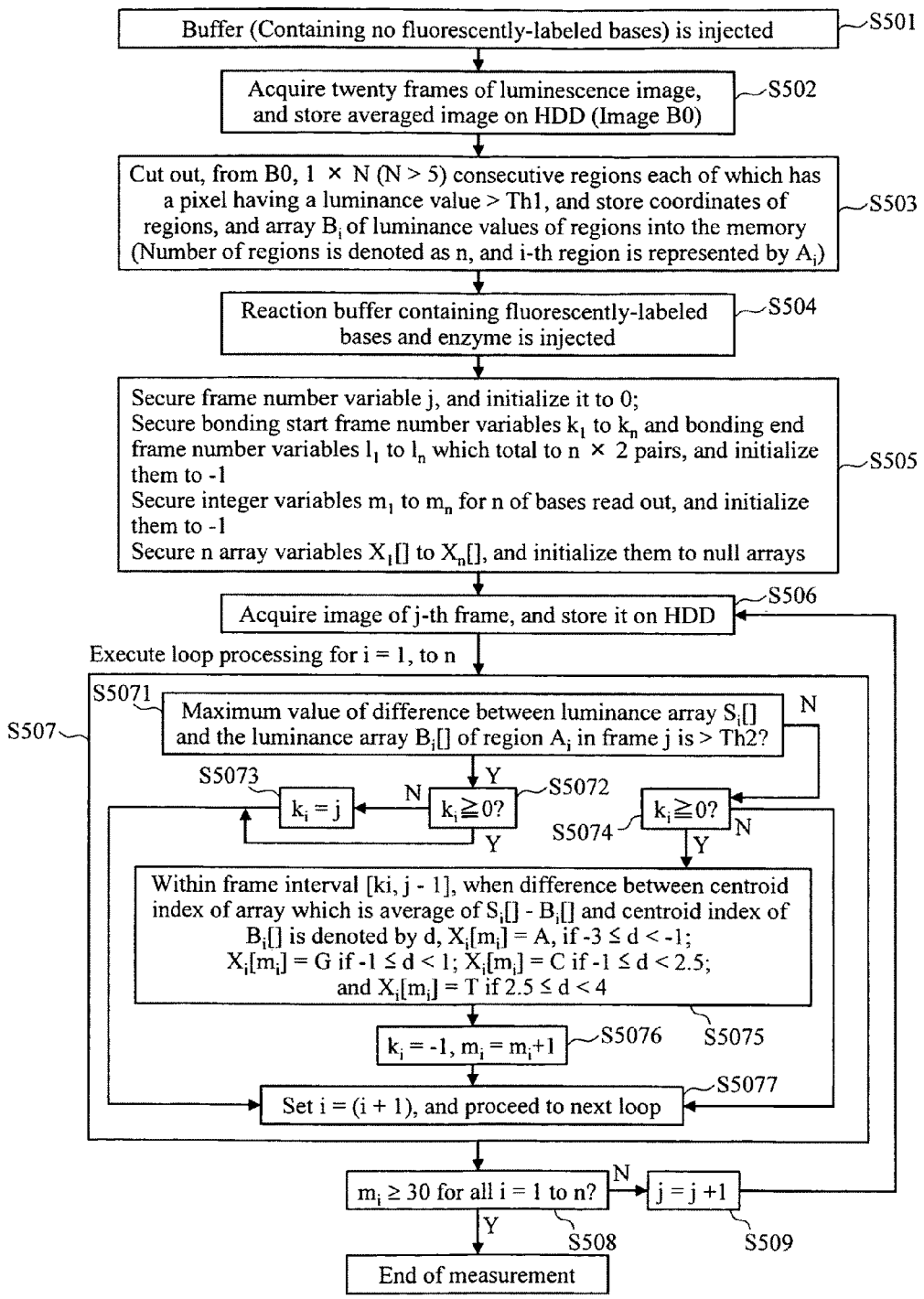
FIG. 5 is a flowchart for explaining base sequence judgment processing.

Luminescence from the surface of the substrate, which is excited by the evanescent waves, is condensed and collimated by an objective lens 7, and thereafter, a component (elastic scattered light) of the luminescence is eliminated by a luminescence filter 8, the component having the same wavelengths as the excitation light. Thereafter, the luminescence is dispersed by a dispersing element 9 toward different directions depending on wavelengths, and then, an image is formed on a photoelectric surface of an image sensor 11 by an imaging lens 10. After undermentioned processing shown in FIG. 5 is executed by a computing unit 20, the image obtained by the image sensor 11 is recorded on a storage device (HDD) 19. Although a second harmonic wave laser of Nd-YAG whose wavelength is 532 nm is used as the excitation source 1 in this embodiment, any one of an argon ion laser, a helium neon laser, a semiconductor laser and the like may be used instead. As the luminescence filter 8, a filter that transmits light having a wavelength of a wavelength of the laser plus α (for example, 5 nm) can be used, and a long pass filter transmitting light having a wavelength of 540 nm or more is used in this embodiment where the Nd-YAG laser is used. Obviously, however, any one of a band pass filter transmitting a range of wavelengths to be detected, and a notch filter blocking only a wavelength of the excitation light can be used. Additionally, although a prism is used as the dispersing element in this embodiment, it is obvious that a diffraction grating is also acceptable.

2. State of Biomolecules in Vicinity of Substrate

Figure 2A:
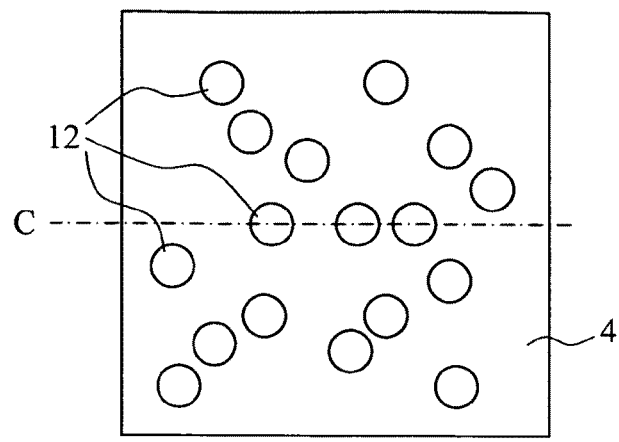
FIGS. 2A and 2B are enlarged views of the vicinity of a substrate in the first embodiment.
Figure 2B:
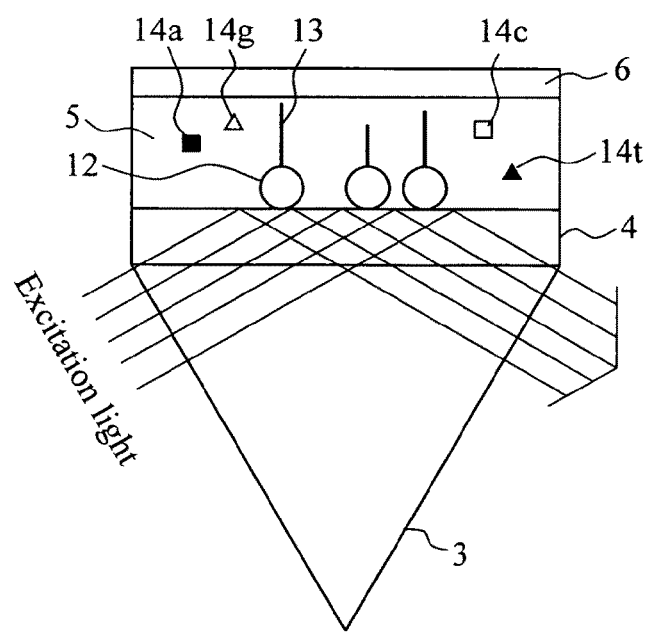

FIGS. 2A and 2B are enlarged views of the vicinity of the substrate 4 of the photometric instrument 100. FIG. 2A is a top view thereof, and FIG. 2B is a cross-sectional view taken along an alternate long and short dash line C. A plurality of particulates 12 on which biomolecules 13 are fixed are fixed on the substrate 4. The fixation of the particulates 12 is achieved, for example, by coating the substrate surface with a surfactant and strewing gold particulates thereon. Although gold particulates each having a diameter of 50 nm are used here as the particulates 12, any metallic particulates made of silver, copper, aluminum, chrome or the like, and each having a diameter not larger than the wavelength of the excitation light are acceptable. Moreover, a form of each of the particulates 12 is not limited to a sphere, and may be any one of a rectangular parallelepiped, a circular cone, a circular cylinder, and another distorted form. Additionally, although the gold particulates are randomly strewed in FIG. 2 in order to inexpensively manufacture the substrate, they may be arranged in a lattice pattern.

In this embodiment, the biomolecules 13 fixed on the particulates 12 are single-stranded DNA, and the reaction solution contains fluorescent-labeled bases 14a, 14g, 14c and 14t, and an enzyme used for causing an extending reaction. For example, the base 14a is adenine labeled with a pigment which becomes luminous by green, the base 14g is guanine labeled with a pigment which becomes luminous by orange, the base 14c is cytosine labeled with a pigment which becomes luminous by red, and the base 14t is thymine labeled with a pigment which becomes luminous by infrared. Every time a complementary strand extends with a base being incorporated into the single-stranded DNA, luminescence corresponding to the base causing the extension is excited on an evanescent field on the substrate, and is emitted from the gold particulates. Although one string of the single-stranded DNA is fixed on each of the particulates 12, it is obvious that a plurality of strings thereof may be fixed thereon, and that two-stranded DNA may be fixed thereon.

3. Dispersion Image of Substrate

Figure 3:
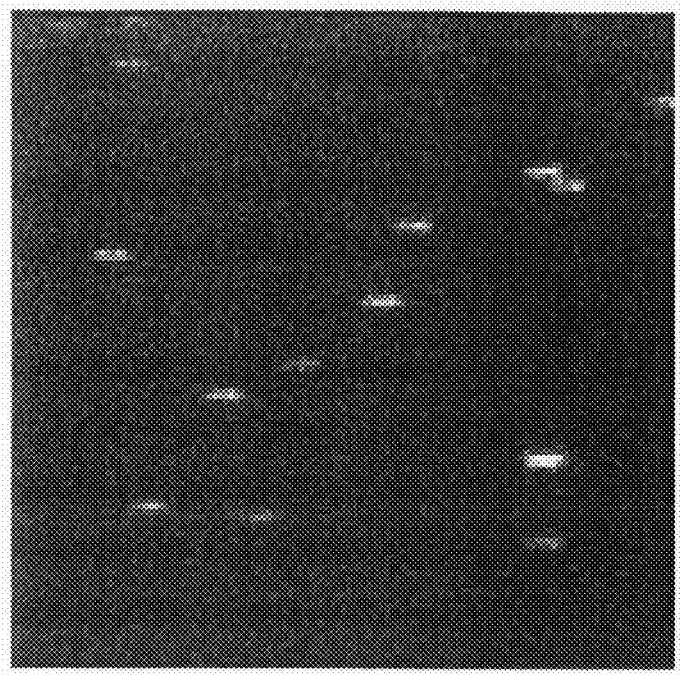
FIG. 3 is a view showing a dispersion image of structures which is obtained in the first embodiment.
Figure 4:
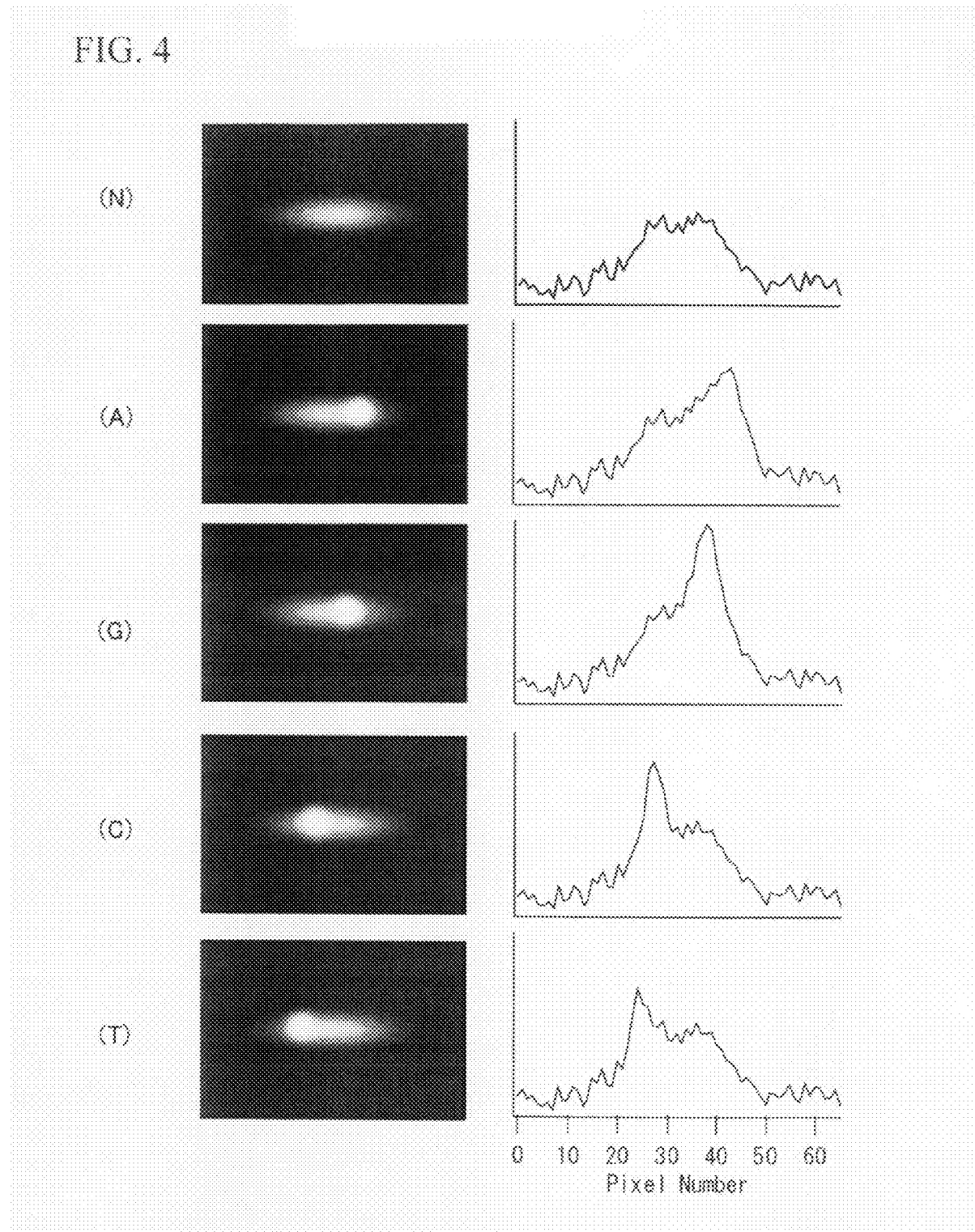
FIG. 4 is an enlarged view of a dispersion image obtained when an extending reaction occur.

FIG. 3 is a view showing a dispersion image of the substrate before the start of the extending reaction. FIG. 4 is a view showing dispersion images of the substrate after the extending reaction.

As shown in FIG. 3, each of the gold particulates emits broad (meaning that a range of the wavelengths is broad) photoluminescence having wavelengths of 500 to 700 nm, whereby spots of the gold particulates, each of which extends in a laterally long and narrow shape, are obtained.

A column in the left-hand side of FIG. 4 shows enlarged views of one gold particle spot, and a column in the right-hand side thereof shows graphs describing luminance profiles in lateral directions of the spot. In FIG. 4, (N) corresponds to when there is only a gold particulate, (A) to when adenine is bonded thereto, (G) to when guanine is bonded thereto, (C) to when cytosine is bonded thereto, and (T) to when thymine is bonded thereto. Note that, in the constitution of this embodiment, the longer a wavelength of light emitted from the same point is, the more left the light is focused. Luminescence of the gold particulate incessantly exists. Therefore, when a base is bonded thereto, the luminescence is observed in a state overlapped with luminescence of a phosphor used for labeling the base, and a part corresponding to a luminous wavelength becomes brighter than when there is only a gold particulate. As a result, from the fact that the part has become brighter, it is found that a base is bonded thereto. Additionally, judgment on a species of the phosphor, that is, a species of the base becomes possible from a relative position of the brighter part with respect to the gold particulate spot.

4. Base Species Judgment Processing

Next, details of base species judgment processing will be described. FIG. 5 is a flowchart showing a detailed algorithm of the base species judgment processing. A program corresponding to FIG. 5 is stored in an unillustrated memory, and the program is executed by the computing unit 20 when the base species judgment processing is executed. Therefore, a subject who executes processing in each step in FIG. 5 is the computing unit 20 unless otherwise stated. Additionally, in FIG. 5, Th1 and Th2 refer to a predetermined threshold value for judging luminescence of the structures, and a predetermined threshold value for judging luminescence of biomolecules, respectively.

In step S501, a solution (a buffer) containing neither the fluorescently-labeled bases nor the enzyme is injected between the substrate 4 and the cover glass 6 by an operator. Then, after preparations for acquiring images of luminescence are completed, an instruction for starting observation is inputted to the computing unit 20 by the operator. In this state, only luminescence from the gold particulates is observed. A single strand of DNA is previously fixed on each of the structures, and there is a double strand formed therein as a result of partial hybridization of this single strand with another single strand having a sequence complementary to the former single strand.

In step S502, for example, twenty frames of luminescence images only of a gold particulate are acquired, and the acquired images are averaged with respect to the time axis.

Because luminescence of gold does not fade, thus averaging a large number of frames (that is, frames obtained by long-time measurement) makes it possible to obtain a favorable S/N ratio even when the luminescence is weak.

In step S503, regions each having luminance values of Th1 or more in at least N laterally consecutive pixels (N>2) are extracted as luminance spots of gold, from an image resulting from the averaging. In this embodiment, N is set greater than 5 because an apical angle of the prism is adjusted so that luminance wavelengths of gold (550 to 700 nm) can be dispersed in six pixels. Here, the number of the extracted regions is denoted by n, and the i-th region thereof and a luminance array thereof are represented by $A_i$ and $B_i$, respectively.

Subsequently, in step S504, the reaction solution (reaction buffer) 5 containing the fluorescently-labeled bases and the enzyme is injected by the operator. Then, after the injection is completed, the instruction for starting observation is inputted to the computing unit 20 by the operator.

In step S505, variables used in subsequent measurement loop steps S506 to S509 are initialized. From this point on, bonding reactions of the bases to the DNA fixed on the gold particulates, and luminescence of phosphors used for labeling begin, and steps S506 to S509 are repeated in the meanwhile until the measurement is completed.

The variables initialized in step S505 are used in the following manner. A frame start number j is a number of accumulated frames of images having been serially acquired after the start of the measurement loop. Additionally, a variable $k_i$ is a variable for storing a number (frame number) assigned to a frame where luminescence of a phosphor has started by boding of a base to the i-th spot $A_i$. A variable $l_i$ is a variable for storing a frame number assigned to a frame where the luminescence of the phosphor has ended by removal of the phosphor from the base having bonded to the i-th spot $A_i$. A variable $m_i$ (i=1 to N) is a variable for storing how many times the bonding and removal of a phosphor is repeated for spot $A_i$. Furthermore, the variable $m_i$ is the number of bases which is read out from the spot $A_i$. Additionally, N arrays $X_i$ for storing base sequences having read out from the respective spot are secured. In the above variables, i equals any one of 1 to N.

In step S506, every time a new frame j is acquired, processing in step S507 is executed to n regions. Hereinbelow, the processing will be described as processing of the i-th region. First of all, if a difference between a luminance array $S_i$ for the region $A_i$ in the latest frame and the already recorded luminance array $B_i$ also for the region $A_i$ with respect to luminescence only of gold has exceeded the predetermined threshold value Th2, it is judged that a phosphor, i.e., some base, is bonded to the i-th spot (step S5071), and the processing proceeds to step S5072. In step S5072, whether $k_i \geq 0$ is judged. If $k_i < 0$, it means that the bonding has not yet occurred in a frame before the latest one. Consequently, the bonding starting frame number $k_i$ is set to j, for it is judged that new bonding has occurred (step S5073). If $k_i \geq 0$, it merely means that a phosphor having bonded in a frame of (j−1) or earlier keeps being luminous. Consequently, $k_i$ is not changed, and the processing proceeds to the processing for the next spot after i is set to (i+1) (step S5077).

On the other hand, in step S5071, when a difference between $S_i$ and $B_i$ is not more than Th2, it is judged that a phosphor is not bonded, whereby the processing proceeds to step S5074. In step S5074, whether $k_i \geq 0$ is judged. If $k_i < 0$, it means that a phosphor has not bonded still since a frame before the latest one. Consequently, the processing proceeds to the processing for the next spot after i is set to (i+1) (step S5077). If $k_i \geq 0$, it is judged that a bonded phosphor is removed. In step S5075, a difference (which becomes a luminance spectrum of the phosphor) between an average value $S_i$ of frames obtained from $k_i$ to j, and $B_i$ is calculated, whereby a difference d between an index which is a centroid of this array, and a centroid index of $B_i$ is found. This d represents a central wavelength of the phosphor luminescence spectrum. Based on properties of phosphors used in this embodiment, the phosphor used for labeling is judged to be: adenine if $-3 \leq d < -1$; guanine if $-1 \leq d < 1$; cytosine if $-1 \leq d < 2.5$; or thymine if $2.5 \leq d < 4$ (step S5075). Thereafter, in step S5076, $m_i$ is set to ($m_i$+1), and a base corresponding to $X[m_i]$ is stored on the storage device 19.

In this embodiment, the fluorescent-labeled bases used are nucleotide triphosphate to which phosphors for the labeling is bonded. An extending reaction is started with a base coming close to the vicinity of the DNA 13, and the phosphor exists in the vicinity of the DNA only until the reaction is completed. At the completion of the extending reaction, the phosphor is cut off from the base along with phosphate, and is swiftly removed from the vicinity of the DNA 13 by Brownian motion. In another method of removing a phosphor after an extending reaction, nucleotide triphosphate, which is fluorescently labeled with 3'OH, is extend, and then after the extending reaction, the phosphor is cut off therefrom through a photochemical reaction caused by ultraviolet laser. According to this method, there is an advantage that timing for removing a phosphor can be controlled. Additionally, it is also possible that, after a main body of a base of nucleotide triphosphate is labeled with a phosphor, a portion corresponding to the phosphor is cut off through a photochemical reaction caused by ultraviolet laser likewise, or is caused to fade before a next base is incorporated.

The abovementioned steps are executed for each frame and for all of the spots, and are repeated until $m_i$ becomes at least 30 (steps S508 and S509). By this processing, sequences of at least 30 bases are read for every one of the spots.

Incidentally, in this embodiment, expression analysis of messenger RNA is set as a target application, and a measurement ending condition is set to $m_i \geq 30$ as it is sufficient to be able to read 30 bases. In a case where application is required to read a longer base length, for example, to read genome for which draft sequences are undecided, it is only necessary to set the measurement ending condition to a larger numeric value, for example, $m_i \geq 100$, $m_i \geq 400$ or the like.

Incidentally, although in present example, the sequencing of a single DNA molecule is performed with the DNA molecule being fixed on each of the structures, it is obvious that the same is possible also with an enzyme being fixed thereon. 5. As described above, according to this embodiment, photo-luminescence from the structures on which biomolecules are fixed is detected in a system based on the dispersive spectral imaging method. Thereby, it becomes possible to perform judgment on a species of a luminous phosphor with high accuracy, the judgment having been conventionally difficult in the dispersive spectral imaging method. As a result, highly accurate sequencing becomes possible.

Second Embodiment

The same constitution as that of the photometric instrument 100 according to the first embodiment can be applied to a photometric instrument according to a second embodiment. Therefore, description regarding the constitution of the instrument will be omitted. Additionally, the same processing as that in the first embodiment can be applied to base species judgment here as well.

Figure 6A:
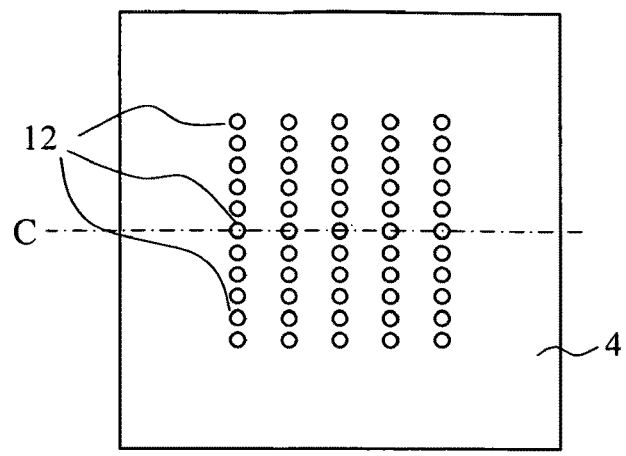
FIGS. 6A and 6B are enlarged views of the vicinity of a substrate in a second embodiment.
Figure 6B:
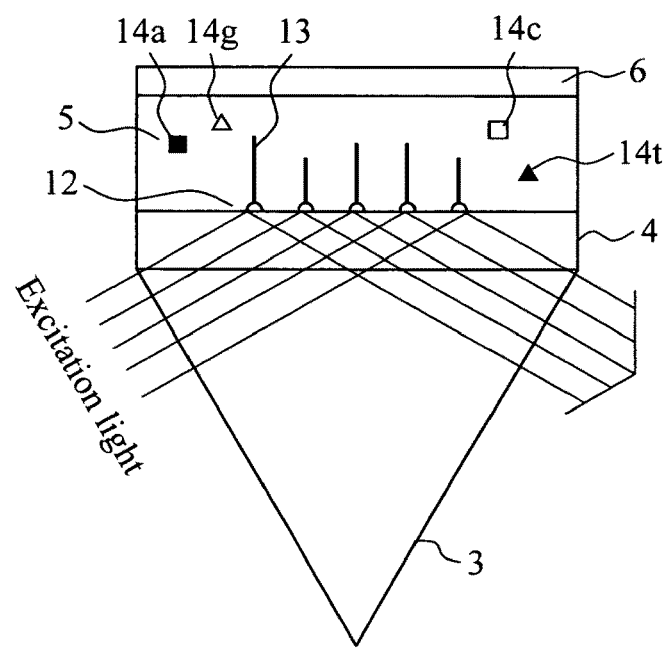

FIGS. 6A and 6B are enlarged views of the vicinity of the substrate 4 in the second embodiment. FIG. 6A is a top view of the substrate, and FIG. 6B is a cross-sectional view taken along an alternate long and short dash line C in FIG. 6A.

In this embodiment, the structures on which biomolecules are fixed are arranged in a lattice pattern by use of a semiconductor process. Furthermore, although EB (electron beam) drawing is used in the manufacturing process here, any one of dry etching and wet etching may be used.

By thus configuring the constitution, the structures (for example, gold particulates) can be integrated on the substrate 4 with high density, whereby a number of the spots processed at one time can be increased. As a result, a processing speed for sequencing is improved.

Third Embodiment

The same constitution as that of the photometric instrument 100 according to the first embodiment can be applied to a photometric instrument according to a third embodiment. Therefore, description regarding the constitution of the instrument will be omitted. Additionally, the same processing as that in the first embodiment can be applied to base species judgment here as well.

Figure 7A:
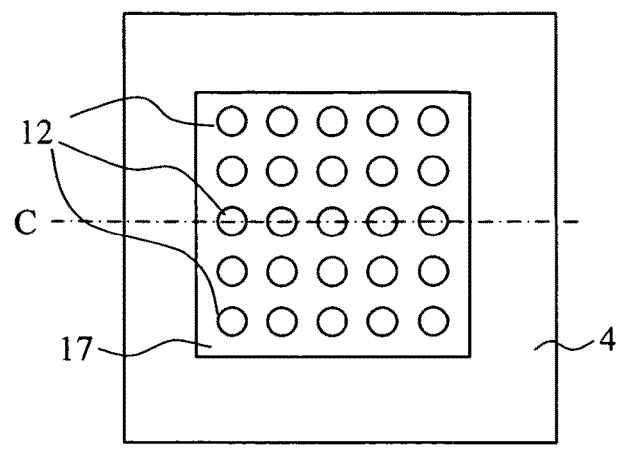
FIGS. 7A and 7B are enlarged views of the vicinity of a substrate in a third embodiment.
Figure 7B:
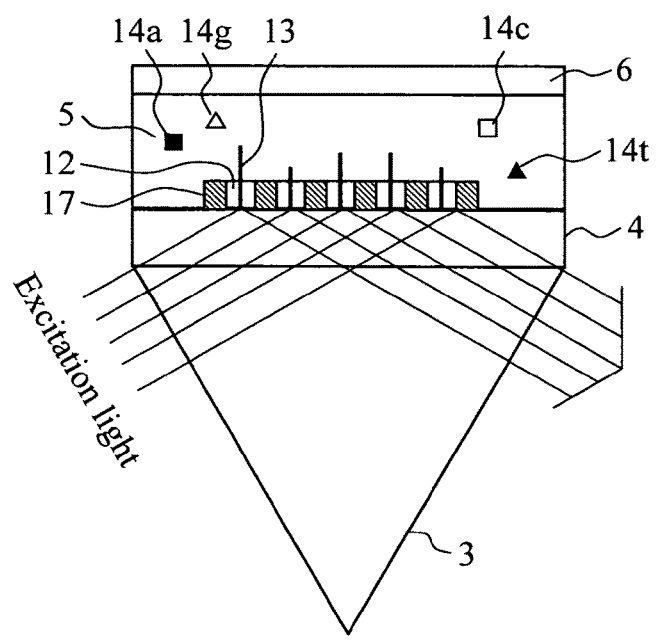

FIGS. 7A and 7B are enlarged views of the vicinity of the substrate 4 in the third embodiment. FIG. 7A is a top view of the substrate, and FIG. 7B is a cross-sectional view taken along an alternate long and short dash line C in FIG. 7A.

In this embodiment, minute apertures provided to a metallic thin film are used as the structures on which biomolecules are fixed. Apertures each having a diameter of 100 nm are provided on an aluminum thin film through EB drawing with 2.3 micron pitches in lateral directions and with 1 micron pitches in longitudinal directions. However, a thin film made of any metal such as gold or chrome can be favorably used, and a diameter of each of the apertures can be set to any value not larger than a wavelength (for example, 532 nm in the abovementioned case where the Nd-YAG laser is used) of the excitation light. Incidentally, a manufacturing process is not limited to EB drawing, and any one of dry etching and wet etching may be used.

By thus configuring the constitution, regions from which evanescent waves are generated are limited to the vicinities of the apertures, and thereby Raman scattering of the reaction solution excited by the evanescent waves occurs only in the vicinities of the apertures (a size of a luminous region is small). Consequently, background light on the substrate 4 is suppressed to be low, and as a result, an S/N ratio of luminescence detection from the phosphors is improved.

Forth Embodiment

Figure 8:
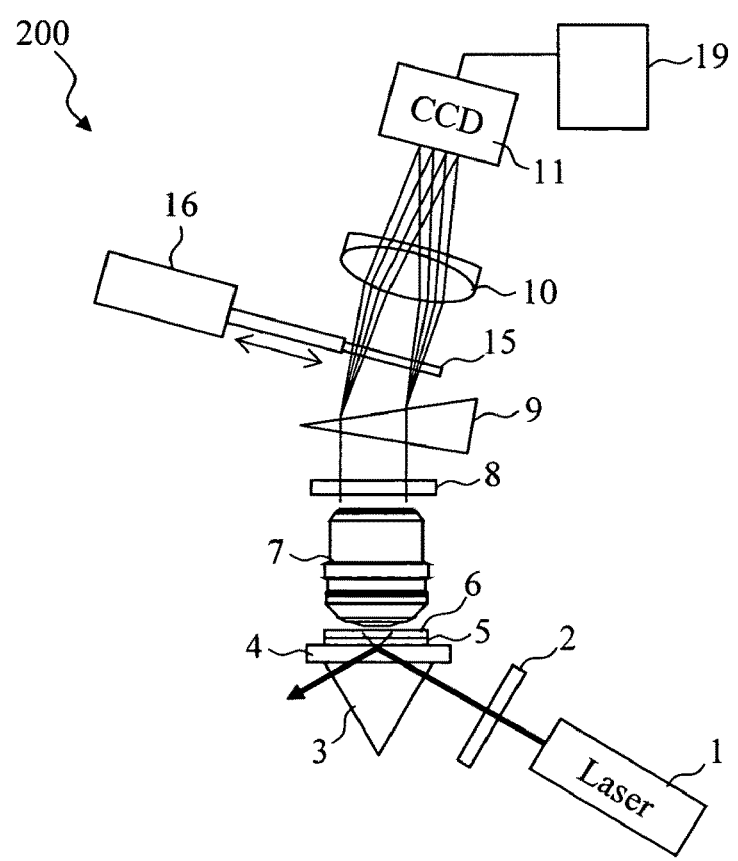
FIG. 8 is a view showing a schematic constitution of a photometric instrument according to a forth embodiment of the present invention.

FIG. 8 is a view showing a schematic constitution of a photometric instrument 200 according to a forth embodiment of the present invention. While a basic constitution of the photometric instrument 200 is almost the same as the first embodiment, a band pass filter 15 is insertable into and removable from an optical path by means of a stage 16. This band pass filter 15 is used to limit luminescence of the structures (for example, gold particulates) to a certain range (a transmission range of the band pass filter) because the luminescence of the structures varies.

The band pass filter is inserted into the optical path at the start of the measurement, and is removed therefrom by means of the stage 16 after several frames of images (images only of the structures) are acquired in an inserted state. In other words, the filter 15 is in a removed state when reactions are caused.

By thus configuring the constitution, there is an effect that a highly accurate wavelength standard can be obtained regardless of variation in the luminance spectrums of the structures.

Incidentally, the fluorescence measurement can be performed also by using a combination of the substrate used in any one of the first to third embodiments and the photometric instrument 200 in this embodiment. Additionally, the same processing as that in the first embodiment can be applied to base species judgment here.

Fifth Embodiment

Figure 9:
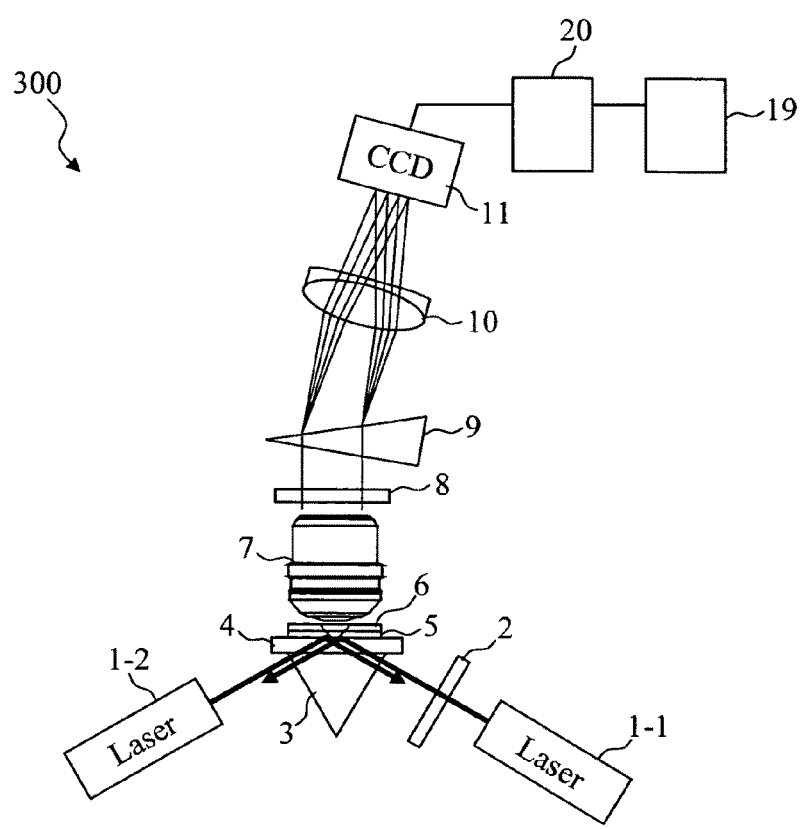
FIG. 9 is a view showing a schematic constitution of a photometric instrument according to a fifth embodiment of the present invention.

FIG. 9 is a view showing a schematic constitution of a photometric instrument 300 according to a fifth embodiment of the present invention. The photometric instrument 300 is provided with a plurality of excitation sources 1-1 and 1-2 which respectively output light having different wavelengths, and a constitution of the photometric instrument 300 except these is the same as the first embodiment.

By thus configuring the constitution, a larger number of phosphor species can be detected with high sensitivity. The reason for this is as follows. Excitation efficiencies are different by phosphor species, and consequently, there is a limit in detecting a larger number of phosphor species in some cases if the detection is performed only by an excitation source having one wavelength.

Incidentally, the fluorescence measurement can be performed also by using a combination of the substrate used in any one of the first to third embodiments and the photometric instrument 300 in this embodiment. Additionally, the same processing as that in the first embodiment can be applied to base species judgment here.

Sixth Embodiment

Figure 10:
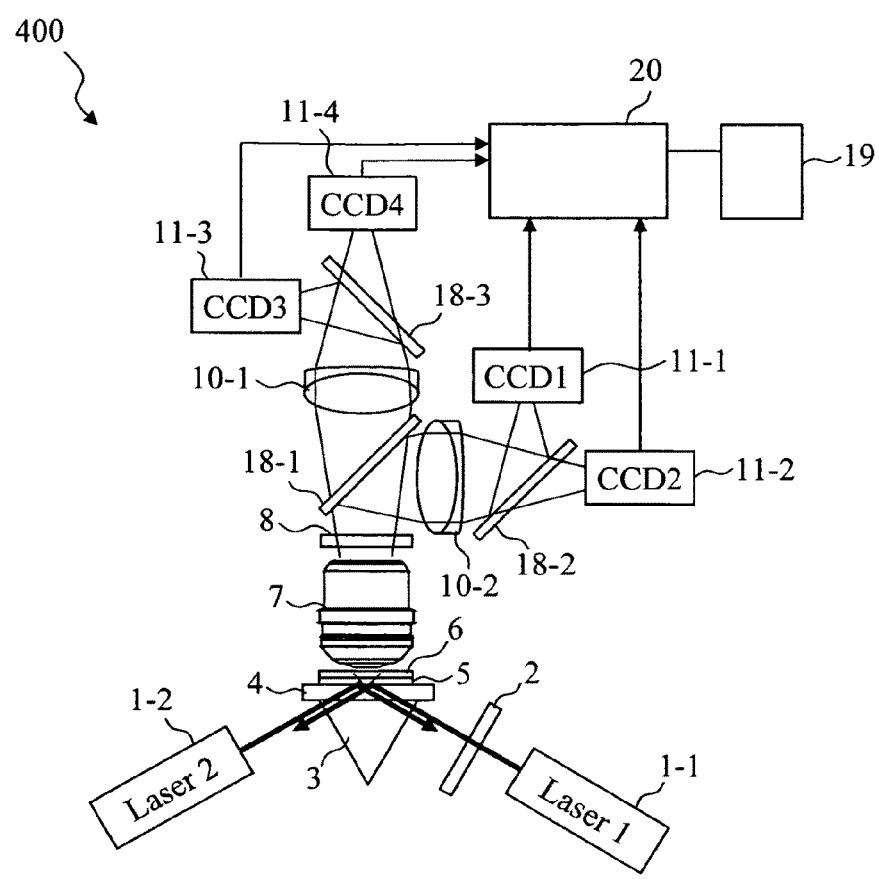
FIG. 10 is a view showing a schematic constitution of a photometric instrument according to a sixth embodiment of the present invention.

FIG. 10 is a view showing a schematic constitution of a photometric instrument 400 according to a sixth embodiment of the present invention. The photometric instrument 400 is provided with the same constitution as the fifth embodiment with respect to components from at least one excitation source (the excitation sources 1-1 and 1-2, or the excitation source 1-1 or 1-2) to the luminescence filter 8. However, a plurality of dichroic mirrors are used as a means for spectrally separating light the instead of dispersing element 9. That is, as shown in FIG. 10, light having passed through the filter 8 is separated into reflected light and transmitted light by a first dichroic mirror 18-1 (which transmits light having a wavelength of 600 nm or more, and reflects light having wavelengths shorter than that). Thereafter, the transmitted light and the reflected light pass through the imaging lens 10-1 and the imaging lens 10-2, respectively. The reflected light is further separated into reflected light and transmitted light by a second dichroic mirror 18-2 (which transmits light having a wavelength of 570 nm or more, and reflects light having wavelengths shorter than that). The reflected light here is detected by a first image sensor 11-1, and the transmitted light here by a second image sensor 11-2.

On the other hand, the transmitted light of the first dichroic mirror 18-1 is further separated into reflected light and transmitted light by a third dichroic mirror 18-3 (which transmits light having a wavelength of 680 nm or more, and reflects light having wavelengths shorter than that). The reflected light here is detected by a third image sensor 11-3, and the transmitted light here by a fourth image sensor 11-4.

Additionally, a substrate which is the same as the substrate used in any one of the first to third embodiments can be used as the substrate 4 in this embodiment.

Figure 11:
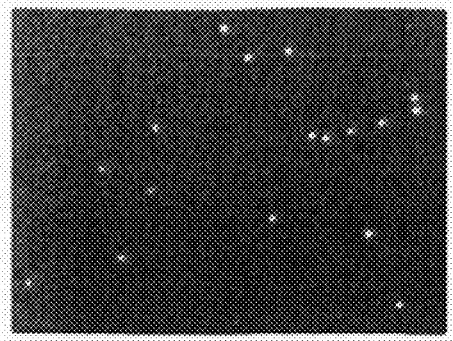
FIG. 11 is a view showing spectral images of structures obtained in the fifth embodiment.
Figure 11:
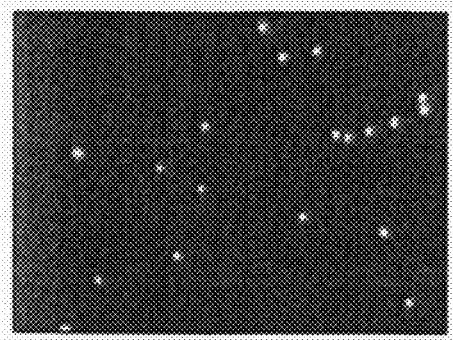
Figure 11:
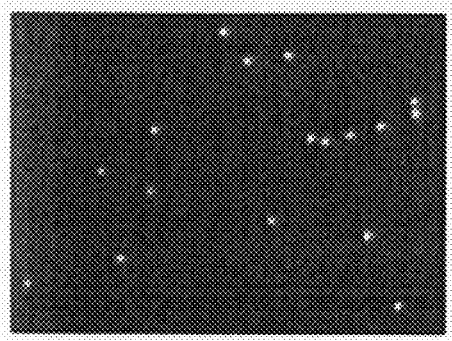
Figure 11:
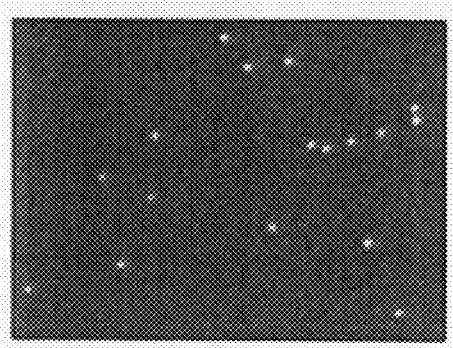

FIG. 11 shows examples of spectral images obtained at the same time by the four image sensors 11-1 to 11-4. Because the luminescence spectrums of the structures are broad as described above, luminescence spots originating from the same structures can be acquired in every one of these images. Without the structures, it is difficult to identify luminescence from the same biomolecule because bright spots are acquired only in one of the images, and are not acquired in the other images. However, as shown in FIG. 11, positions in which luminescence spots are to be generated when phosphors have bonded can be found beforehand by the luminescence from the structures. Consequently, it becomes possible to identify luminescence from the same biomolecule with high accuracy, and as a result, possible to perform sequencing with high accuracy.

As described above, in this embodiment, a spot in an image does not spread out to be laterally long (refer to FIG. 3) because light is not dispersed by a dispersing element. Consequently, overlapping of spots does not occur, and it becomes possible to integrate biomolecules on the substrate with high density. Additionally, it is also possible to perform position alignment by using (1) to (4) of FIG. 11. Incidentally, the same processing as that in the first embodiment can be applied to base species judgment here.

Seventh Embodiment

Figure 12:
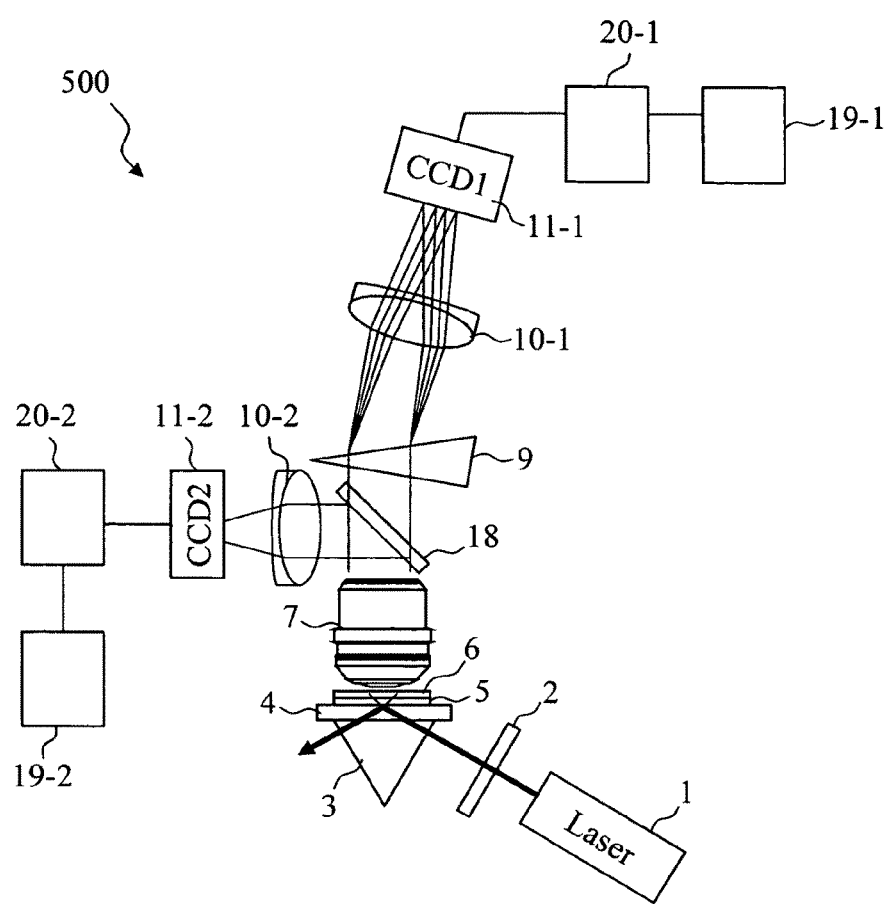
FIG. 12 is a view showing a schematic constitution of a photometric instrument according to a seventh embodiment of the present invention.

FIG. 12 is a view showing a schematic constitution of a photometric instrument 500 according to a seventh embodiment of the present invention. In the photometric instrument 500, elastic scattered light from the substrate 4 is not blocked by the filer 8, and reflected by a dichroic mirror 18. The reflected light forms an image on the second image sensor 11-2 through a second imaging lens 10-2. A constitution of the photometric instrument 500 except that is the same as that of the photometric instrument 100 in the first embodiment.

By thus configuring the constitution, it becomes possible to judge phosphor species based on images obtained by the second image sensor 11-2 even if dispersion images of the structures, which are obtained by the first image sensor 11-1, overlap one another and end up being inseparable between each structure. That is, one piece of an image including only the structures (for example, gold particulates) shown in FIG. 11 for example is obtained by the second image sensor 11-2, so that positions of the structures can be determined. Consequently, sharp distinctions are made between images of the structures based on images obtained by the second image sensor 11-2, even if, as shown in FIG. 3, spots of the structures become laterally so long that adjacent ones of the spot images overlap one another in images obtained by the image sensor 11-1.

Accordingly, there is an effect that the biomolecules 13 can be more densely integrated on the substrate 4 than in the first embodiment. Moreover, elastic scattered light has a strong intensity. This eliminates the need to use a highly sensitive cooled CCD camera as a second image sensor, and makes it possible to use uncooled CCD, CMOS sensor and the like which are inexpensive. Consequently, a substantial cost increase is not brought about as compared to the first embodiment. Incidentally, the same processing as that in the first embodiment can be applied to base species judgment.

Eighth Embodiment

While the same constitution as that of the photometric instrument 100 according to the first embodiment is applied to a photometric instrument according to an eighth embodiment, an elastic-scattered-light blocking capability of the filter 8 is lowered. Thereby, dispersion images of photoluminescence of the structures and an image of elastic scattered light are overlapped with one another on the image sensor 11 to form an image thereon. For example, in the eighth embodiment, this is realized by using only one filter having a light transmittance factor of $1/1000$ instead of using two of them as in the case with the first embodiment, or by using a filter having a light transmittance factor of $10^{-4}$ to $10^{-5}$.

Figure 13A:
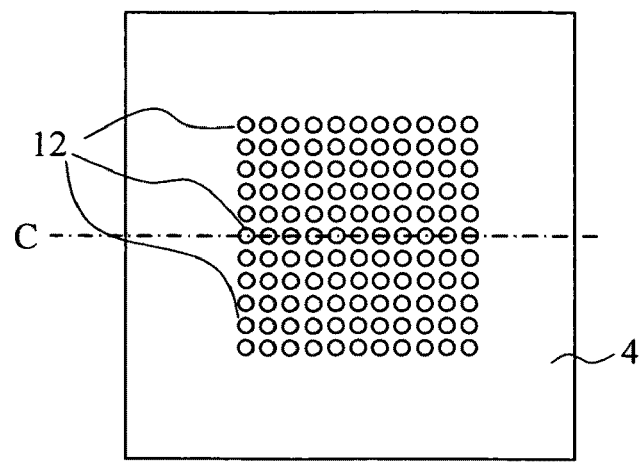
FIGS. 13A and 13B are enlarged views of the vicinity of a substrate in an eighth embodiment.
Figure 13B:
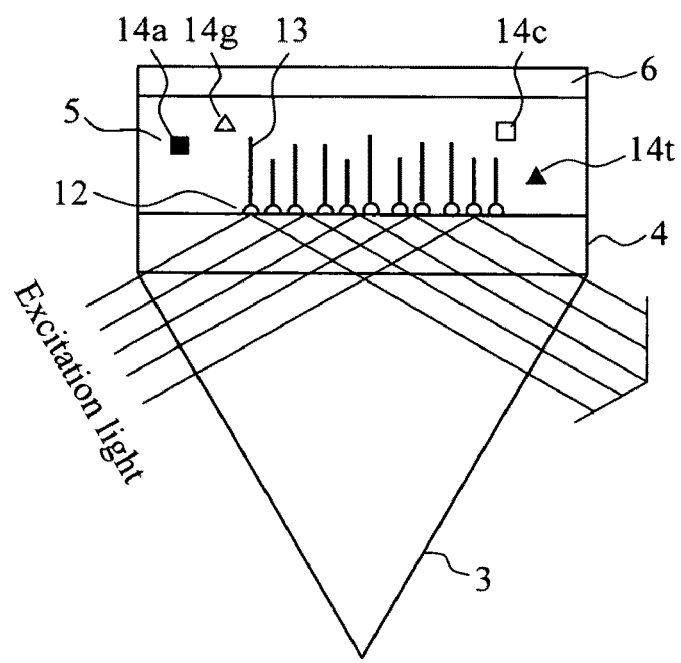

FIGS. 13A and 13B show enlarged views of the substrate 4 in the eighth embodiment. In this embodiment, the structures are integrated with 1 μm pitches both laterally and longitudinally.

Because the structures are thus integrated with 1 μm pitches on the substrate 4 both laterally and longitudinally, dispersion images of long-wavelength components from the structures are connected with each other, and end up being perceived only as continuous background light.

Figure 14:
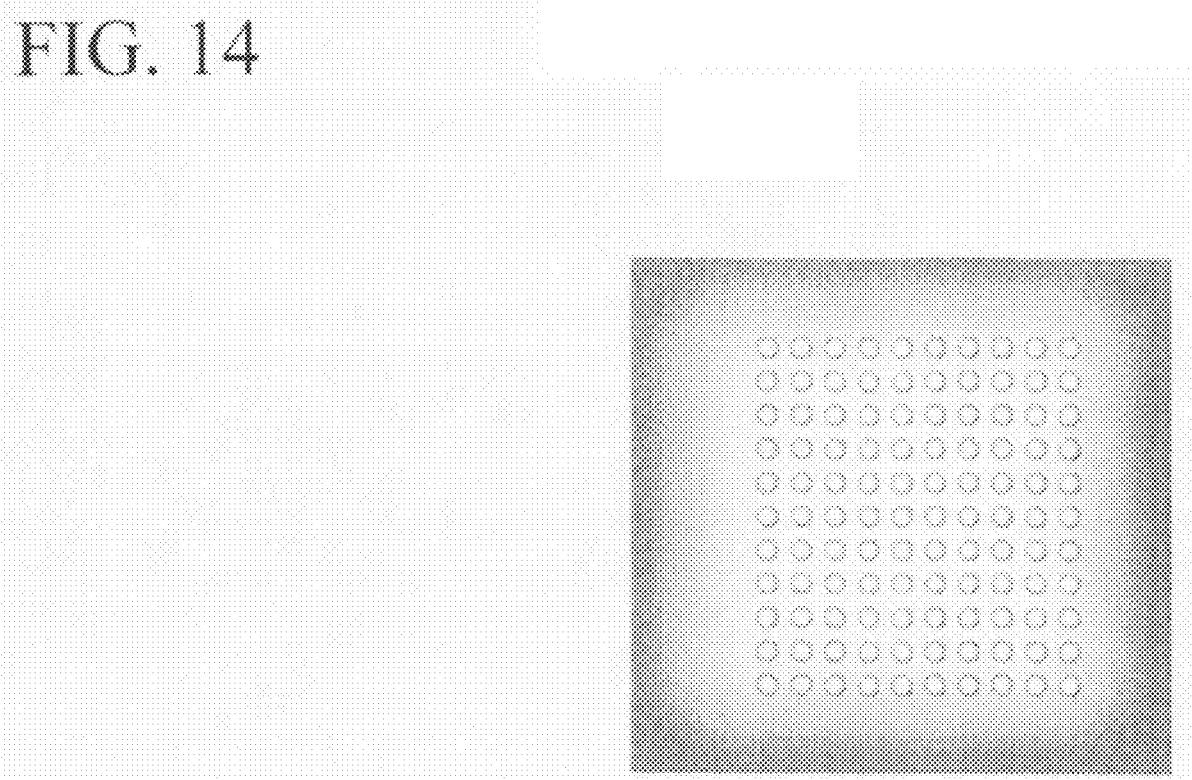
FIG. 14 is a view showing a dispersion image of a substrate obtained in the eighth embodiment

As shown in FIG. 14, however, because elastic scattered light is partially transmitted, sharp elastic-scattered-light images of the structures are formed on the connected dispersion images. As a result, it becomes possible to identify phosphor species based on the elastic scattered light images even if the dispersion images are overlapped with each other. Accordingly, the same effect as in the case with the seventh embodiment can be obtained. Moreover, only one image sensor is necessary, and the blocking capability of the filter can be made low. Consequently, cost is decreased while fluorescence images having higher S/N ratios can be obtained. Incidentally, the same processing as that in the first embodiment can be applied to base species judgment.

Ninth Embodiment

While the same constitution as that of the photometric instrument 300 according to the fifth embodiment is applied to a photometric instrument according to a ninth embodiment, this photometric instrument is characterized in that; a wavelength of the light source 1-2 is in a transmission range of the filter 8; and light outputted by the light source 1-2 and then scattered by the structures 12 is detected. Specifically, a HeNe laser of a wavelength of 594 nm is adopted as the light source 1-2. Otherwise, any one of a HeNe laser of a wavelength of 633 nm, and any semiconductor laser can be favorably used. The laser of a wavelength of 532 nm, which is the same as the light source 1 of the first embodiment, can be used as an light source 1-2, if the transmission range of the filter 8 is changed to 520 nm or more, and if the light source 1-1 changed to an argon ion laser of a wavelength of 488 or 514.5 nm. Additionally, a power of the light source 1-2 is allowed to be far smaller than that of the light source 1-1, whereby it is also possible to favorably use a light-emitting diode having the wavelength of the transmission range of the filter 8. This embodiment has a characteristic effect that wavelength standard is highly accurate since the scattered light is substantially monochromatic. Additionally, the power of the light source 1-2 is allowed to be small, and a cost increase is not substantially brought about as a result of increasing a number of light sources to two.

The present invention is applied to a DNA sequencer utilizing extending reactions, a DNA microarray reader using a total reflection fluorescence method, and the like.

REFERENCE NUMERALS 1, 1-1, 1-2 excitation source
2 excitation filter
3 prism
4 substrate
5 reaction solution
6 cover glass
7 objective lens
8 luminescence filter
9 dispersing element
10, 10-1, 10-2 imaging lens
11, 11-1 to 11-4 image sensor
12 structure
13 biomolecule
14a adenine
14g guanine
14c cytosine
14t thymine
15 band pass filter
16 stage
18, 18-1 to 18-3 dichroic mirror
19 storage device
20 computing unit

What is claimed is:

1. A photometric instrument, comprising:
a substantially transparent substrate provided with a plurality of metal structures on each of which a biomolecule is fixed;
at least one light source for irradiating the substrate with excitation light so as to generate evanescent waves from the substrate;
a light separating portion for spectrally separating light emitted from the structures;
a sensor portion for detecting both luminescence from the structures and luminescence from the structures with a biomolecule being fixed on the structures, the luminescence from the structures having a part with longer wavelengths than the excitation light; and
a processing portion for generating positional information of the structures based on the difference between luminescence only from the structures and luminescence from the structures with a bonded biomolecule on said structures.

2. The photometric instrument according to claim 1, further comprising a second light source for irradiating the substrate with light having a longer wavelength than the excitation light.

3. The photometric instrument according to claim 1, wherein, based on the light spectrally separated, the sensor portion collectively detects images of the plurality of structures fixed on the substrate.

4. The photometric instrument according to claim 1, wherein each of the structures is a metallic structure of a size not larger than a wavelength of the excitation light.

5. The photometric instrument according to claim 1, wherein,
the substrate includes a metallic thin film, and
each of the structures is an aperture formed in the metallic thin film on the substrate, the aperture having a diameter not larger than a wavelength of the excitation light.

6. The photometric instrument according to claim 1, wherein the light separating portion is constituted of a dispersing element.

7. The photometric instrument according to claim 1, wherein,
the light separating portion is constituted of a plurality of dichroic mirrors, and
the sensor portion is constituted of a plurality of image sensors.

8. The photometric instrument according to claim 1, wherein the processing portion computes a difference between a first image detected when the biomolecule is not luminous and a second image detected when the biomolecule is luminous, and then compares this difference and the first image to determine a species of the biomolecule having become luminous.

9. The photometric instrument according to claim 1, wherein
the sensor portion detects light resulting from overlapping of light emitted from the structures with light emitted from the biomolecules, and
the processing portion generates the positional information by using the light resulting from the overlapping.

10. The photometric instrument according to claim 9, wherein the processing portion determines a species of the biomolecules based on relative positions of parts in the light resulting from the overlapping, the parts being brighter than surroundings thereof.

11. A photometric instrument, comprising:
a substantially transparent substrate provided with a plurality of metal structures on each of which a biomolecule is fixed;
at least one light source for irradiating the substrate with excitation light so as to generate evanescent waves from the substrate;
a light separating portion for spectrally separating light emitted from the structures;
a sensor portion for detecting both luminescence from the structures and luminescence from the structures with a biomolecule being fixed on the structures, the luminescence from the structures having a part with longer wavelengths than the excitation light and a part with the same wavelength as the excitation light,
a processing portion for generating positional information of the structures based on the luminescence from the structures having a part with longer wavelengths than the excitation light and a part with the same wavelength as the excitation light.

12. The photometric instrument according to claim 11, wherein, based on the light spectrally separated, the sensor portion collectively detects images of the plurality of structures fixed on the substrate.

13. The photometric instrument according to claim 11, wherein each of the structures is a metallic structure of a size not larger than a wavelength of the excitation light.

14. The photometric instrument according to claim 11, wherein,
the substrate includes a metallic thin film, and
each of the structures is an aperture formed in the metallic thin film on the substrate, the aperture having a diameter not larger than a wavelength of the excitation light.

15. The photometric instrument according to claim 11, wherein the light separating portion is constituted of a dispersing element.

16. The photometric instrument according to claim 11, wherein
the light separating portion is constituted of a plurality of dichroic mirrors, and
the sensor portion is constituted of a plurality of image sensors.

17. The photometric instrument according to claim 11, wherein the processing portion computes a difference between a first image detected when the biomolecule is not luminous and a second image detected when the biomolecule is luminous, and then compares this difference and the first image to determine a species of the biomolecule having become luminous.

18. The photometric instrument according to claim 11, wherein the sensor portion detects light resulting from overlapping of light emitted from the structures with light emitted from the biomolecules; and the processing portion generates the positional information by using the light resulting from the overlapping.

19. The photometric instrument according to claim 18, wherein the processing portion determines a species of the biomolecules based on relative positions of parts in the light resulting from the overlapping, the parts being brighter than surroundings thereof.

* * * * *